United States Patent [19]

Suh et al.

[11] Patent Number: 4,569,941
[45] Date of Patent: Feb. 11, 1986

[54] METHOD OF USING PHENYL-ALKYLENE-2-PYRIDYL DERIVATIVES TO INCREASE CARDIAC CONTRACTILITY IN A MAMMAL

[75] Inventors: John T. Suh, Greenwich, Conn.; Rack H. Chung, deceased, late of Clifton Park, Clifton Park, N.Y., by Betsy Y. Chung, executrix; Nai-Yi Wang, East Windsor, N.J.; Jeffrey N. Barton, New York, N.Y.

[73] Assignee: USV Pharmaceutical Corp., Tarrytown, N.Y.

[21] Appl. No.: 692,602

[22] Filed: Jan. 17, 1985

Related U.S. Application Data

[63] Continuation of Ser. No. 477,460, Mar. 21, 1983, abandoned.

[51] Int. Cl.$^4$ ............................................. A61K 31/445
[52] U.S. Cl. ..................................... 514/317; 514/331
[58] Field of Search ....................... 424/256, 263, 267; 514/277, 317, 331

[56] References Cited

U.S. PATENT DOCUMENTS 3,910,934 10/1975 Sankey et al. ...................... 424/267
3,941,796  3/1976 Sankey et al. ...................... 424/267
4,342,692  8/1982 Suh et al. .......................... 424/267

FOREIGN PATENT DOCUMENTS 0595631  1/1948 United Kingdom ................ 424/267

OTHER PUBLICATIONS

Hoffmann–La Roche, Inc., CA, vol. 42, p. 3437, 1948.

Primary Examiner—Henry R. Jiles
Assistant Examiner—J. G. Mullins

[57] ABSTRACT

Compounds of the formulae:

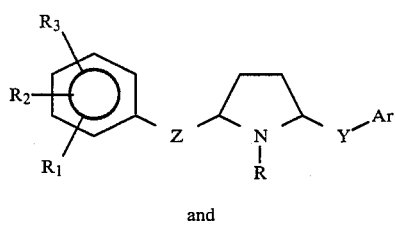

and

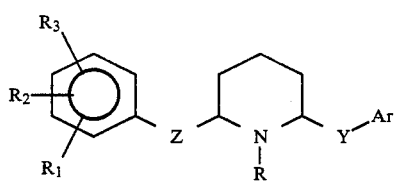

wherein,

Z and Y are each alkylene or oxy-alkylene containing one to about five carbon atoms in the principal chain or said alkylene substituted with OH, alkanoyloxy, alkoxy, mercapto or alkylmercapto;

each of $R_1$, $R_2$ and $R_3$ is independently H, alkyl, aryl, halo, alkoxy, alkenyloxy, alkylsulfinyl, alkylsulfonyl, alkylmercapto, cyano, carboxy, carbalkoxy, carboxamido, sulfamoyl, trifluoromethyl, hydroxy, hydroxyalkyl, acyloxy, alkylamino, sulfonylamino, or acylamino; or $R_1$ and $R_2$, when taken together, form a methylenedioxy or —O—CO—O—;

Ar is heteroaryl, cycloalkyl or

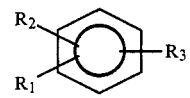

wherein, $R_1$, $R_2$ and $R_3$ are as hereindescribed; and R is H, alkyl, cycloalkyl, aryl, aralkyl, alkenyl, alkynyl, carboalkoxy, or $CONR_4R_5$ wherein each of $R_4$ and $R_5$ is H or alkyl; wherein the total number of carbon atoms in each hydrocarbyl group is up to 10; and

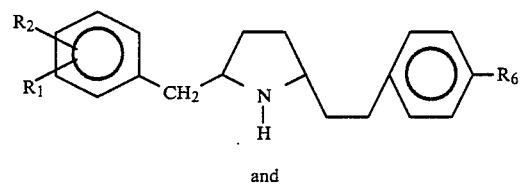

and

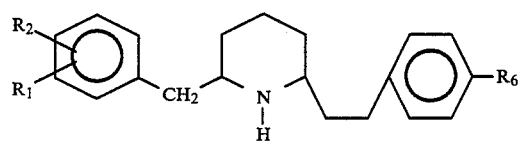

wherein, each of $R_1$ and $R_2$ is independently H, alkyl, aryl, halo, alkoxy, alkenyloxy, alkylsulfinyl, alkylsulfonyl, alkylmercapto, cyano, carboxy, carbalkoxy, carboxamido, sulfamoyl, trifluoromethyl, hydroxy, hydroxyalkyl, acyloxy, alkylamino, sulfonylamino, or acylamino; or $R_1$ and $R_2$, when taken together, form a methylenedioxy, or —O—CO—O—; $R_6$ is H, alkyl, aryl, halo, alkoxy, alkenyloxy, alkylsulfonyl, alkylmercapto, cyano, carboxy, carbalkoxy, carboxamido, sulfamoyl, trifluoromethyl, hydroxy, hydroxyalkyl, acyloxy, alkylamino, sulfonylamino or acylamino; wherein the total number of carbon atoms in each hydrocarbyl group is up to 10; and acid addition salts thereof have selective cardiotonic, antihypertensive and antiallergic activity.

4 Claims, No Drawings

METHOD OF USING PHENYL-ALKYLENE-2-PYRIDYL DERIVATIVES TO INCREASE CARDIAC CONTRACTILITY IN A MAMMAL

RELATED APPLICATIONS

This application is a continuation of our copending application Ser. No. 477,460 filed Mar. 21, 1983, now abandoned.

This invention relates to new pharmaceutically-active compounds and more particularly to certain new cyclic amines possessing useful pharmaceutical activities, especially selective cardiotonic activity, anti-hypertensive activity and anti-allergic activity.

Pharmaceutically-active amines of the formula:

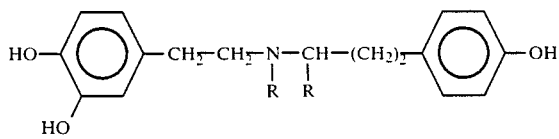

wherein R is hydrogen or alkyl have been described in German Patent Specification No. 2,317,710. These compounds are reported to have cardiotonic activity.

The new compounds of the present invention are cyclic amines of the formulae:

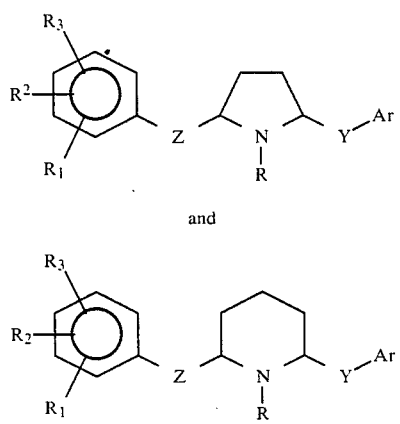

wherein,

Z and Y are each alkylene or oxy-alkylene containing one to about five carbon atoms in the principal chain or said alkylene substituted with OH, alkanoyloxy, alkoxy, mercapto or alkylmercapto;

each of $R_1$, $R_2$ and $R_3$ is independently H, alkyl, aryl, halo, alkoxy, alkenyloxy, alkylsulfinyl, alkylsulfonyl, alkylmercapto, cyano, carboxy, carbalkoxy, carboxamido, sulfamoyl, trifluoromethyl, hydroxy, hydroxyalkyl, acyloxy, alkylamino, sulfonylamino, or acylamino; and $R_1$ and $R_2$, when taken together, form a methylenedioxy or —O—CO—O—;

Ar is heteroaryl, cycloalkyl, alkyl or

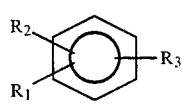

wherein, $R_1$, $R_2$ and $R_3$ are as hereindescribed; and

R is H, alkyl, cycloalkyl, aryl, aralkyl, alkenyl, alkynyl, carboalkoxy, or $CONR_4R_4$ wherein each of $R_4$ and $R_5$ is H or alkyl;

and acid addition salts thereof.

The total number of carbon atoms in each such hydrocarbyl substituent can range up to about 10. The substituent "Z" contains up to about 5 carbon atoms in the principal chain, i.e., the straight chain of carbons between the terminal valences, but can be branched in that methyl and ethyl substituents can be present on the principal chain. Thus, the Z chain can contain a total number of carbon atoms greater than 5, preferably no more than about 8.

Heteroaryl as employed herein refers to any heterocyclic structure in which at least one of O, S and N are present as the hetero atoms. These include thiophene, furan, pyridine, thiazole, pyimidine, pyrrole, benzofuran, quinoline, benzothiophene and substituted heterocycles.

The preferred compounds are those in which the hydrocarbyl radicals contain up to about 7 carbon atoms when aliphatic and up to about 10 carbon atoms when aromatic, e.g., phenyl, tolyl and naphthyl.

The particularly preferred compounds are cyclic amines of the formulae:

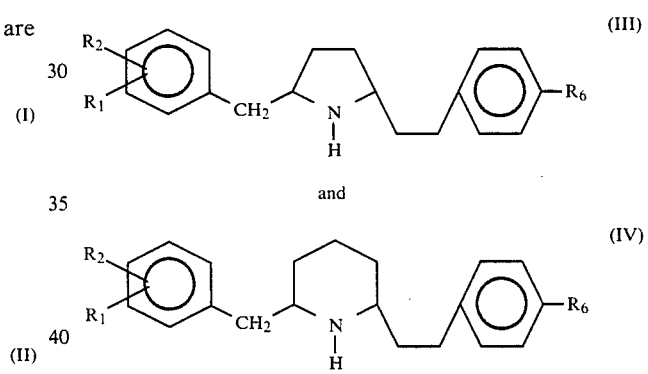

wherein, $R_1$ and $R_2$ are as previously defined; and $R_6$ is H, alkyl, aryl, halo, alkoxy, alkenyloxy, alkylsulfonyl, alkylmercapto, cyano, carboxy, carbalkoxy, carboxamido, sulfamoyl, trifluoromethyl, hydroxy, hydroxyalkyl, acyloxy, alkylamino, sulfonylamino or acylamino; and acid addition salts thereof.

In particular, the preferred compounds are of the structure

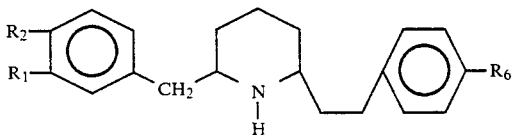

wherein $R_1$, $R_2$ and $R_6$ are hydroxy or alkanoyloxy and may be the same or different, the alkyl portion in the alkanoyloxy having up to 6 carbon atoms.

As should be apparent to those skilled in the art, the present new compounds exist in isomeric forms due to the spatial arrangement of substituents at the positions ortho to the nitrogen atom in the cyclic amine, i.e., cis and trans forms; and can also exist in the form of optical isomers when there are asymmetric centers, e.g., as in substituents Z and Y. The present new compounds include all of the isomeric forms, in particular, the cis, trans-isomers, both of which can be present in the products as produced by the synthetic process selected for preparation. The mixtures of isomers are useful as are the individual, i.e., separated, isomers for therapy.

The present new compounds are readily preparable by art-recognized procedures. A particularly effective procedure involves reduction of the corresponding new dehydro-cyclic amines of the formulae:

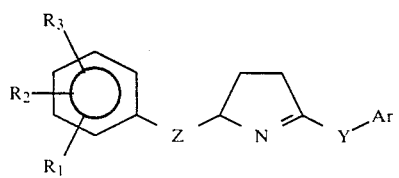

and

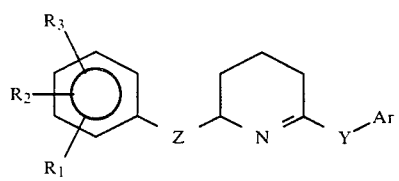

wherein, $R_1$, $R_2$, $R_3$, Z, Y and Ar are as previously defined. Of course, substituents susceptible of reduction under the process conditions can be converted to their corresponding reduction product, e.g., nitro to amino.

The new intermediate compounds of formula V and VI can also be prepared by art-recognized methods. The following reaction sequence employing pyrrolidine derivatives is exemplary;

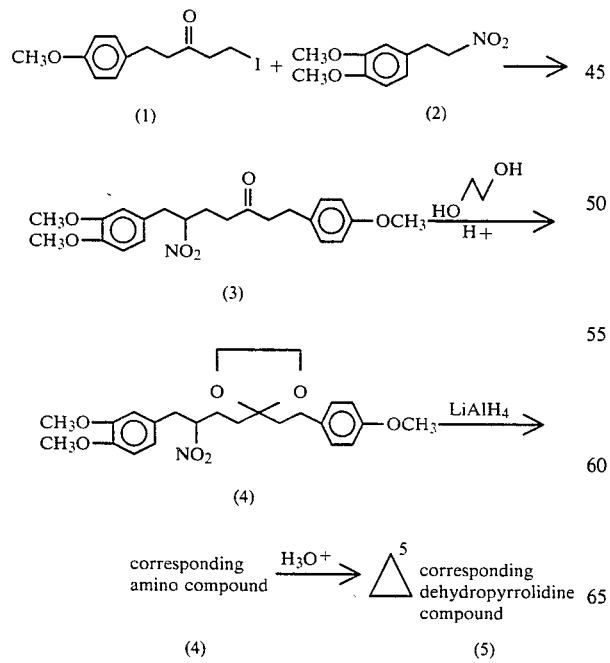

Each of the steps of the foregoing sequence is accomplished using known procedures as described in the examples which follow. The hydrogenation step to convert compounds of formulae V and VI to corresponding compounds of formulae I and II can be accomplished using any of the known processes for reducing an ethylenic double bond. The most common and facile of these is catalytic hydrogenation, e.g., over noble metal catalysts such as palladium or platinum catalysts. Such catalytic hydrogenations are normally effected at superatmospheric pressures of hydrogen gas, e.g., 3 to 20 atmospheres, until the theoretical uptake of hydrogen has occurred. For efficiency, the hydrogenation is carried out in a solvent such as tetrahydrofuran, dioxane and the like.

The compounds wherein R is other than hydrogen may be prepared from the compounds where R is hydrogen by standard technique for the alkylation or acylation of an amine.

Of particular value are the compounds wherein $R_1$ and $R_2$ are acyloxy. These compounds are preferably prepared from the compounds wherein $R_1$ and $R_2$ are methoxy by the following sequence of reactions:

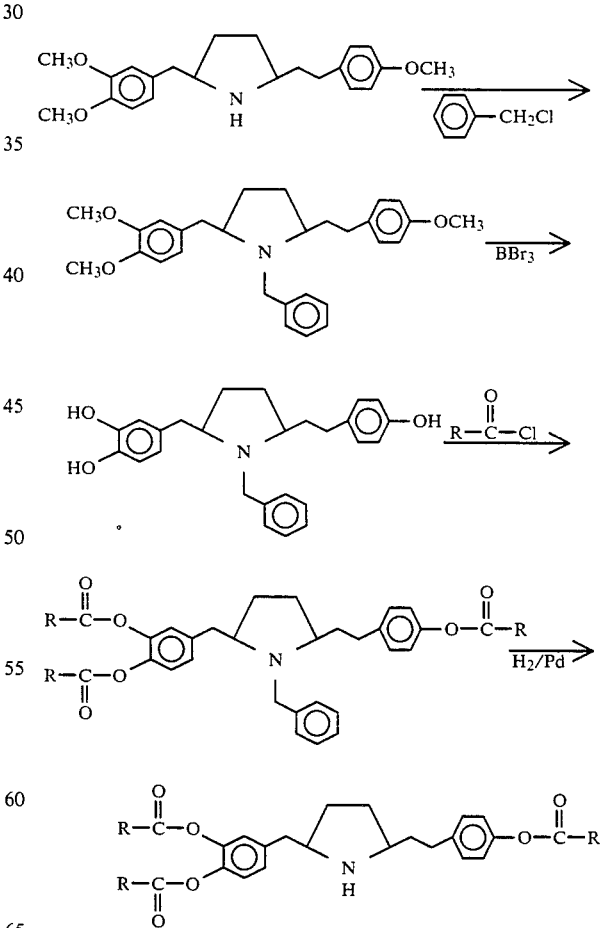

Methods for the preparation of other compounds of the present invention are outlined below:

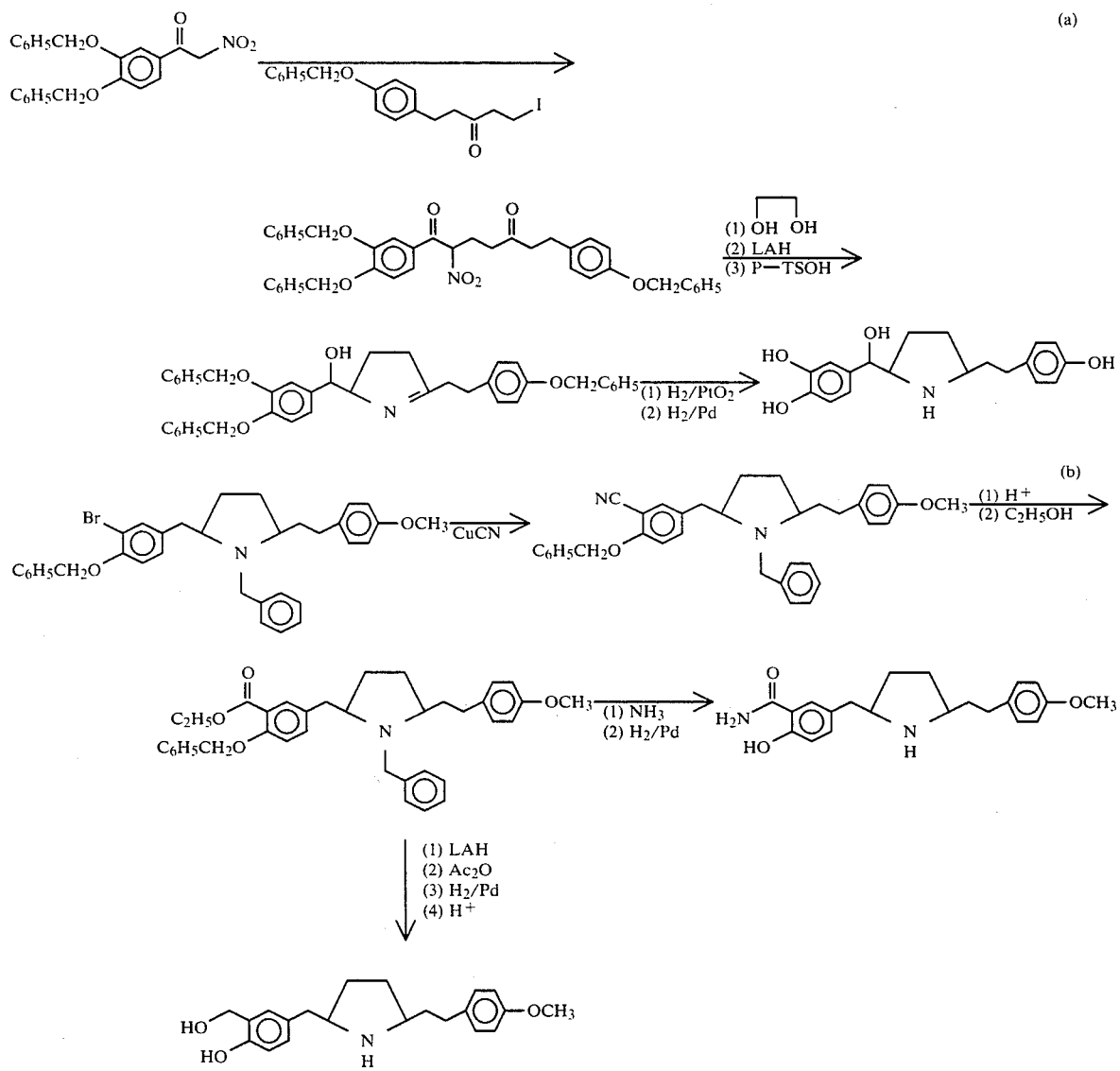

Employing the foregoing procedures, a variety of new pyrrolidine and piperidine compounds of formulae I and II can be prepared:

| Z | R | Y | $R_1$ | $R_2$ | $R_3$ | Ar |
|---|---|---|---|---|---|---|
| CHCH$_3$ | CH$_3$ | C$_2$H$_4$ | H | H | H | C$_6$H$_5$ |
| CHCH$_3$ | CH$_3$ | C$_2$H$_4$ | H | CH$_3$ | H | C$_6$H$_5$ |
| CH$_2$CH$_2$ | CH$_3$ | C$_2$H$_4$ | H | H | H | C$_6$H$_4$Cl |
| CH(CH$_3$)CH$_2$ | C$_2$H$_5$ | C$_2$H$_4$ | H | H | Cl | C$_6$H$_4$CH$_3$ |
| CH$_2$CH$_2$ | CH$_3$ | i-C$_3$H$_6$ | H | CN | H | C$_4$H$_3$S |
| CH$_2$CH$_2$ | CH$_3$ | C$_2$H$_4$ | H | H | NO$_2$ | C$_4$H$_3$O |
| CH$_2$CH$_2$ | CH$_3$ | C$_2$H$_4$ | H | OH | H | C$_5$H$_4$N |
| CH$_2$CH$_2$ | C$_3$H$_7$ | CH$_2$ | H | H | CF$_3$ | C$_3$H$_2$NS |
| CH(CH$_3$) | C$_4$H$_9$ | C$_2$H$_4$ | H | OCH$_3$ | H | C$_6$H$_5$CH$_2$ |
| (CH$_2$)$_3$ | C$_6$H$_{13}$ | C$_2$H$_4$ | H | COOH | H | C$_6$H$_5$ |
| CH$_2$CH$_2$ | i-C$_4$H$_9$ | CH$_2$ | OCH$_3$ | H | H | ClC$_6$H$_4$ |
| CH$_2$CH$_2$ | H | C$_2$H$_4$ | H | OCH$_3$ | OCH$_3$ | MeOC$_6$H$_4$ |
| (CH$_2$)$_5$ | C$_6$H$_5$CH$_2$ | C$_2$H$_4$ | H | CH$_3$ | CH$_3$ | C$_6$H$_4$OH |
| CH$_2$CH$_2$ | C$_6$H$_{11}$ | C$_2$H$_4$ | H | H | CH$_2$C$_6$H$_5$ | C$_6$H$_4$OH |
| CH$_2$CH$_2$ | H | C$_2$H$_4$ | H | H | C(CH$_3$)$_3$ | C$_6$H$_4$OH |
| CH(CH$_3$)CH$_2$ | C$_6$H$_5$ | C$_2$H$_4$ | H | H | C$_6$H$_5$ | C$_6$H$_4$OH |
| CH$_2$ | H | C$_2$H$_4$ | H | H | H | C$_6$H$_4$OH |
| CH$_2$ | H | C$_2$H$_4$ | Cl | Cl | Cl | C$_6$H$_4$OH |
| CH$_2$ | H | C$_2$H$_4$ | Cl | H | Cl | C$_6$H$_4$OH |
| CH$_2$ | H | C$_2$H$_4$ | Cl | H | OH | C$_6$H$_4$OH |
| CH$_2$ | H | C$_2$H$_4$ | OCH$_3$ | H | CH$_2$=CH—CH$_2$ | C$_6$H$_4$OH |

-continued

| Z | R | Y | $R_1$ | $R_2$ | $R_3$ | Ar |
|---|---|---|---|---|---|---|
| CH$_2$ | H | C$_2$H$_4$ | H | H | H | C$_6$H$_4$OCH$_3$ |
| CHOH | H | C$_2$H$_4$ | H | CH$_3$ | H | C$_6$H$_4$OCH$_3$ |
| CHOH | H | C$_2$H$_4$ | OH | OH | H | C$_6$H$_4$OCH$_3$ |
| CHOH | H | C$_2$H$_4$ | H | H | H | C$_6$H$_4$OCH$_3$ |
| CHSH | H | C$_2$H$_4$ | H | CH$_3$ | H | C$_6$H$_4$OCH$_3$ |
| CHOCH$_3$ | H | C$_2$H$_4$ | H | CH$_3$ | CH$_3$ | C$_6$H$_4$OCH$_3$ |
| CHSCH$_3$ | H | C$_2$H$_4$ | H | H | H | C$_6$H$_4$OCH$_3$ |
| CHOH | H | C$_2$H$_4$ | H | H | H | C$_6$H$_4$OCH$_3$ |
| CHOCOCH$_3$ | H | C$_2$H$_4$ | H | CH$_3$ | H | C$_6$H$_4$OCH$_3$ |
| CH$_2$CH$_2$ | H | C$_2$H$_4$ | H | H | Cl | C$_6$H$_3$(OH)$_2$ |
| CH$_2$CH$_2$ | H | C$_2$H$_4$ | H | CN | H | C$_6$H$_3$(OH)$_2$ |
| CH$_2$CH$_2$ | H | C$_2$H$_4$ | NO$_2$ | H | H | C$_6$H$_3$(OH)$_2$ |
| CH$_2$CH$_2$ | H | C$_2$H$_4$ | H | OH | H | C$_6$H$_4$OH |
| CH$_2$CH$_2$ | H | C$_2$H$_4$ | H | CF$_3$ | H | C$_6$H$_4$OH |
| CH$_2$CH$_2$ | H | C$_2$H$_4$ | H | OCH$_3$ | H | C$_6$H$_4$OH |
| CH$_2$CH$_2$ | H | C$_2$H$_4$ | H | COOH | H | C$_6$H$_4$OH |
| CH$_2$CH$_2$ | H | C$_2$H$_4$ | OCH$_3$ | H | H | C$_6$H$_4$OH |
| CH$_2$CH$_2$ | H | C$_2$H$_4$ | H | OCH$_3$ | OCH$_3$ | C$_6$H$_4$OH |
| CH$_2$CH$_2$ | H | C$_2$H$_4$ | H | H | OCH$_3$ | C$_6$H$_4$OH |
| CH$_2$CH$_2$ | H | C$_2$H$_4$ | OCH$_3$ | H | CH$_2$=CH—CH$_2$— | C$_6$H$_4$OH |
| CH$_2$CH$_2$ | H | C$_2$H$_4$ | H | H | COOCH$_3$ | C$_6$H$_4$OH |
| CH$_2$CH$_2$ | H | C$_2$H$_4$ | OCH$_3$ | H | COOCH$_3$ | C$_6$H$_4$OH |
| CH$_2$CH$_2$ | H | C$_2$H$_4$ | H | OH | CH$_2$OH | C$_6$H$_4$OH |
| CH$_2$CH$_2$ | H | C$_2$H$_4$ | H | H | NH$_2$ | C$_6$H$_4$OH |
| CH$_2$ | H | C$_2$H$_4$ | H | OCCH$_2$C(CH$_3$)$_3$ (O) | OCCH$_2$C(CH$_3$)$_3$ (O) | C$_6$H$_4$OCCH$_2$C(CH$_3$)$_3$ (O) |
| CH$_3$ | H | C$_2$H$_4$ | H | OH | SOCH$_3$ | C$_6$H$_4$OH |
| CHOH | H | C$_2$H$_4$ | H | OH | SOCH$_3$ | C$_6$H$_3$(OCH$_2$O)— |
| CHOH | H | C$_2$H$_4$ | H | OH | CONH$_2$ | C$_6$H$_3$(OCH$_2$O)— |
| CHOH | H | C$_2$H$_4$ | H | OH | CH$_2$OH | C$_6$H$_4$OH |
| CH$_2$ | H | C$_2$H$_4$ | H | OH | NHSO$_2$CH$_3$ | C$_6$H$_4$OH |
| CHOH | H | C$_2$H$_4$ | H | OH | NHSO$_2$CH$_3$ | C$_6$H$_4$OH |

The present new cyclic amines are therapeutically useful as such or can be employed in the form of salts in view of their basic nature. Thus, these compounds form salts with a wide variety of acids, inorganic and organic, including therapeutically-acceptable acids. The salts with therapeutically-acceptable acids are, of course, useful in the preparation of formulations where water solubility is desired. The salts with therapeutically-unacceptable acids are particularly useful in the isolation and purification of the present new compounds. Therefore, all acid salts of the present new compounds are contemplated by the present invention.

The pharmaceutically-acceptable acid addition salts are of particular value in therapy. These include salts of mineral acids such as hydrochloric, hydriodic, hydrobromic, phosphoric, metaphosphoric, nitric, sulfuric acids, as well as salts of organic acids such as tartaric, acetic, citric, malic, benzoic, glycolic, gluconic, succinic, arylsulfonic, e.g., p-toluenesulfonic acids, and the like. The pharmaceutically-unacceptable acid addition salts, while not useful for therapy, are valuable for isolation and purification of the new substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the new products.

As therapeutic agents, the present new heterocyclic compounds show potent selective cardiotonic activities. In addition, these compounds are also useful as antihypertensive agents and anti-allergic agents. The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk, sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents. The therapeutic dosage will generally be from 10 to 750 milligrams per day and higher although it may be administered in several different dosage units. Tablets containing from 10 to 250 mg. of active agent are particularly useful.

The following examples further illustrate the invention.

EXAMPLE 1

Preparation of dehydro compounds (Formulae V and VI)

A. 1-(3,4-Dimethoxyphenyl)-2-nitroethane

In a 1 l. r.b. flask 100 g. (0.6 mole) of 3,4-dimethoxybenzaldehyde, 40 g. (0.52 mole) of ammonium acetate, 50 ml. (0.93 mole) of nitromethane, and 400 ml. of glacial acetic acid were combined and refluxed for 2 hours. The solution was then cooled to room temperature overnight. Yellow crystals were then collected via suction filtration and washed with hexane and ether. 73 g. of desired product were collected with m.p. 133°–134° C.

B. 1-(3,4-Dimethoxyphenyl)-nitroethane

To a 1 l. 3-necked r.b. flask equipped with mechanical stirrer and thermometer, and cooled in an icewater bath 32 g. (0.847 mole) of $NaBH_4$ pellets and 300 ml. of ethanol were added. The reaction solution was stirred and cooled to 3° C. before the portionwise addition of 21 g. (0.1 mole) of 1-(3,4-dimethoxyphenyl)-2-nitroethene was started. The nitro alkene was added at such a rate as to keep the temperature of the reaction less than 13° C. The resulting solution was stirred an additional 30 min. at ice bath temperature upon the completion of addition.

The foamy solution was then poured into 400 ml. of ice-cold 10% $NH_4Cl$ solution and stirred until the effervesence had subsided. This solution was filtered and concentrated in vacuo to remove the ethanol. Crystallization of 1-(3,4-dimethoxyphenyl)-2-nitroethane occured in the aqueous solution, or the oily product was extracted with ether (3×250 ml.), dried over anhydrous $MgSO_4$ and concentrated to give 20 g. of crystalline product with m.p. 47°–50°.

C. 4-Methoxybenzyl bromide

To a cold solution of 138.17 g. (1 mole) of 4-methoxybenzyl alcohol in 1000 ml. of dry ether was added dropwise 135.35 g. (0.5 mole) of phosphorus tribromide keeping temperature below 10° C. After addition of $PBr_3$ was completed, the mixture was stirred at room temperature for one hour and 30 min. The resulting reaction solution was poured into icewater with agitation, and the product was extracted with ether, which was dried over anhydrous $MgSO_4$ and anhydrous potassium carbonate. Upon removing ether in vacuo, a slightly pinkish crude product was distilled at 89°–90° C./0.15 mm./Hg. yielding 186 g. of 4-methoxybenzyl bromide.

D. Ethyl 4-(4-Methoxybenzyl)acetoacetate

Into a 3 l. 3-necked r.b. flask equipped with a mechanical stirrer, thermometer, dropping funnel, and nitrogen gas inlet was placed 24 g. (0.5 mole) of 50% NaH prewashed with hexane, and 1000 ml. of dry tetrahydrofuran. 65 g. (0.5 mole) of ethyl acetoacetate was then added dropwise at −10° to 0° C. using a dry ice-acetone bath. After addition of ethyl acetoacetate was finished, the mixture was gradually warmed up to 10° C. in the course of 15 minutes and then 240 ml. (0.528 mole) of 2.2M n-butyllithium was added dropwise maintaining temperature below −40° to −20° C. After the mixture was stirred at −10° for 15 minutes, 100.5 g. (0.5 mole) of 4-methoxybenzyl bromide was added dropwise over a period of 45 minutes at −10° C. The reaction mixture was gradually warmed up to room temperature and stirred for an additional hour, and then cooled to −20° C. 5N HCl was then carefully added until the solution was slightly acidic.

The product was extracted with ether several times and ether layer was dried over anhydrous $MgSO_4$. After the solvent was distilled, the crude product was used for the next reaction without purification.

E. Ethyl 5-(4-Methoxyphenyl)-3,3-ethylenedioxypentanoate

The above crude keto ester was ketallized with 100 ml. of ethylene glycol, 2 g. of p-toluenesulfonic acid, and 800 ml. of benzene using a Dean-Stark Trap until no more water was separated. The cooled reaction mixture was poured into a cold dilute $NaHCO_3$ solution and extracted with ether several times. The combined ether layer was backwashed with water once, and dried over anhydrous $MgSO_4$. The product was distilled at 155°–167° C./0.25 mm Hg. to give 97 g. of ketal ester.

F. 3,3-Ethylenedioxy-5-(4-methoxyphenyl)-1-pentanol

Into a 2 l. 3-necked r.b. flask equipped with mechanical stirrer, reflux condenser, and heating mantle was added 18 g. (0.474 mole) of $LiAlH_4$ and 500 ml. of dry tetrahydrofuran at such a rate as to control vigorous reflux of reaction solution. 97 g. (0.33 mole) of ethyl 5-(4-methoxyphenyl)-3,3-ethylenedioxypentanoate in 100 ml. of dry tetrahydrofuran and added dropwise over a period of 40 minutes. The reaction mixture was stirred at room temperature for 30 minutes and refluxed for 2 hrs. Excess $LiAlH_4$ was carefully decomposed with saturated $Na_2SO_4$ solution. The inorganic solid was filtered off and washed with ethyl acetate. The filtrate was concentrated in vacuo leaving 84.6 g. of crude ketal alcohol.

G. 3,3-Ethylenedioxy-5-(4-methoxyphenyl)-1-pentyl methanesulfonate

A solution of 65.9 g. (0.262 mole) of crude ketal alcohol in 250 ml. of pyridine was cooled in an ice bath. 60 g. (0.524 mole) of methanesulfonyl chloride was added dropwise. The mixture was stirred at ice bath temperature for 30 minutes, then for one hour at room temperature, and poured into ice containing 200 ml. of conc. HCl. The pinkish white solid was collected by filtration, washed with cold water, and dried under vacuum at room temperature to leave 89.8 g. of mesyl compound.

H. 1-Iodo-5-(4-methoxyphenyl)-3-pentanone

A mixture of 89.8 g. (0.272 mole) of mesylated derivative, 122.4 g. (0.816 mole) of sodium iodide, and 1000 ml. of acetone was refluxed for 2 hours with stirring. The resulting mixture was poured into 2 l. of water containing 10 g. of sodium sulfite. The light yellowish solid was filtered; washed with water, and dried in vacuum to give 75 g. of product which melts at 38°–42° C.

I. 1-(3,4-Dimethoxyphenyl)-7-(4-methoxyphenyl)-2-nitro-5-heptanone

To a solution of 15 g. (0.071 mole) of 2-(3,4-dimethoxyphenyl)-1-nitroethane in 200 ml. of dry tetrahydrofuran was added 33.45 g. (0.08 mole) of 40% Triton B at room temperature. The solution was stirred at room temperature for 14 minutes under $N_2$. 22.6 g. (0.071 mole) of 1-iodo-5-(4-methoxyphenyl)-3-pentanone was then added in portions. The mixture was heated at 50°-55° for 2 hours under $N_2$ until no more starting material was detected on TLC, and then cooled to room temperature. The resulting reaction solution was poured into cold dil. HCl and extracted with ethyl acetate. The organic layer was dried over anhydrous $MgSO_4$. The crude material was chromatographed on Florisil to provide 22 g. of desired nitro ketone derivative. Recrystallization from 80% ethanol gave a white solid which has m.p. 87°-89° C.

J.
1-(3,4-Dimethoxyphenyl)-5,5-ethylenedioxy-7-(4-methoxyphenyl)-2-nitroheptane Into a 1 l. r.b. flask equipped with a Dean-Stark trap was placed 22 g. (0.055 mole) of 1-(3,4-dimethoxyphenyl)-7-(4-methoxyphenyl)-2-nitro-5-heptanone, 2 g. of p-toluenesulfonic acid, 25 ml. of ethylene glycol, and 500 ml. of benzene, the mixture was refluxed until no more water was separated, and then cooled to room temperature. The dark solution was poured into cold dil. $NaHCO_3$ solution and extracted with ethyl acetate. The organic layer was backwashed with water and dried over anhydrous $MgSO_4$. Upon removing solvent by distillation a gray solid was obtained from trituration with ether. Recrystallization from 80% ethanol yielded 25 g. of product as a white solid; m.p. 98°-100° C.

K.
2-Amino-1-(3,4-dimethoxyphenyl)-5,5-ethylenedioxy-7-(4-methoxyphenyl)heptane To a suspension of 6.6 g. (0.174 mole) of $LiAlH_4$ in 200 ml. of dry tetrahydrofuran was added dropwise a solution of 25 g. (0.058 mole) of 1-(3,4-dimethoxyphenyl)-5,5-ethylenedioxy-7-(4-methoxyphenyl)-2-nitroheptane in 100 ml. of dry THF at room temperature at such a rate as to control reflux of reaction solution. After addition of substrate was completed, the reaction mixture was refluxed under $N_2$ for 2 hours, and cooled to ice bath temperature. The excess $LiAlH_4$ was decomposed with saturated $Na_2SO_4$ solution. The inorganic salt was filtered off and thoroughly washed with ethyl acetate and chloroform. The filtrate was concentrated in vacuo to give 28 g. of brown, oily product. Without further purification, the amino ketal derivative was used for the next reaction.

L.
2-(3,4-Dimethoxybenzyl)-5-[2-(4-methoxyphenyl)ethyl]-$\Delta^5$-dehydropyrrolidine A mixture of 28 g. (0.07 mole) of crude 2-amino-1-(3,4-dimethoxphenyl)-5,5-ethylenedioxy-7-(4-methoxyphenyl)heptane and 12 g. of p-toluenesulfonic acid in 250 ml. of regular tetrahydrofuran was stirred at room temperature for 12 hours under $N_2$. The resulting reaction solution was poured into cold dil. $NaHCO_3$ solution and extracted with ethyl acetate several times. The organic layer was dried over anhydrous $MgSO_4$. The solvent was removed in vacuo to provide 23 g. of brown, oily product which was purified on a dry-column using $CHCl_3$-EtOAc (1:1) as the eluent.

EXAMPLE 2
Production of cyclic amines (Formulae I and II)

A. A mixture of 2,5-cis and trans-2-(3,4-dimethoxybenzyl)-5-[2-(4-methoxyphenyl)ethyl]pyrrolidine hydrochloride Reduction of 23 g. (0.065 mole) of 2-(3,4-dimethoxybenzyl)-5-[2-(4-methoxyphenyl)ethyl]-$\Delta^5$-dehydropyrrolidine in 200 ml. of methanol was carried out in a Parr hydrogenator in the presence of 670 mg. of $PtO_2$ and 40 ml. of ethanolic hydrogen chloride at 65 psi over 2 days. The catalyst was removed on a Celite bed. Upon removing the solvent in vacuo, 19 g. of gray product was obtained from ethyl acetate as the hydrochloride salt; m.p. 156°-161° C.

b.
Cis-2-(3,4-dihydroxybenzyl)-5-[2-(4-hydroxyphenyl)ethyl]-pyrrolidine hydrobromide To a cold solution of 3 g. (0.008 mole) of cis-2-(3,4-dimethoxybenzyl)-5-[2-(4-methoxyphenyl)ethyl]pyrrolidine hydrochloride in 50 ml. of methylene chloride was added dropwise 8 g. (0.032 mole) of boron tribromide at −60° C. After addition of boron tribromide was finished, the cold bath was removed, and the reaction mixture was gradually warmed up to room temperature over a period of about one and a half hours. The mixture was then cooled again in a Dry Ice-Acetone bath and 25 ml. of methanol was carefully added. After methanol was completely removed, the residue was treated with ethyl acetate. Upon storing in a freezer, an off-white solid crystallized out, which was recrystallized from ethyl acetate and ethanol to give 3.11 g. of pure product, m.p. 195°-198° C.

C.
Trans-2-(3,4-dihydroxybenzyl)-5-[2-(4-hydroxphenyl)ethyl]pyrrolidine hydrobromide A solution of 1 g. (0.003 mole) of trans-2-(3,4-dimethoxybenzyl)-5-[2-(4-methoxyphenyl)ethyl]pyrrolidine hydrochloride in 35 ml. of methylene chloride was cooled to −65° C. and treated with 2.68 g. (0.012 mole) of boron tribromide dropwise. The reaction mixture was then stirred under $N_2$ and slowly warmed from −65° to room temperature over the course of one hour and 25 minutes. The solution was then cooled again to −60° C. and 25 ml. of methanol was cautiously added. Solvent was removed in vacuo, more methanol was added and some insoluble material was filtered off. After removal of methanol in vacuo, the residue was treated with ethyl acetate. Upon standing at room temperature, 0.8 g. of product was obtained as an off-white solid, m.p. 202°-203° C.

EXAMPLE 3
1-(3,'4'-Dimethoxyphenyl)-2-nitro-7-(4'-methylphenyl)-3-heptanone ethylene ketal In a 500 mL rb flask, 200 mL cyclohexane, 50 mL benzene, 15 g (0.242 mole) ethylene glycol, 1.5 g p-toluenesulfonic acid and 19 g (0.049 mole) of 1-(3,4-dimethoxyphenyl)-2-nitro-7-(4-methylphenyl)-5-heptanone were combined and refluxed 24 hours with a Dean-Stark trap. The cooled reaction mixture was poured into cold, sat'd. $NaHCO_3$ and extracted with three 200 mL portions of ethyl acetate. The organic layer was dried over $MgSO_4$, filtered and concentrated. The residue was triturated with ether and ethyl acetate to give some solid (1.5 g) of mp 89°–91° C.

The remaining residue was chromatographed on silica gel using hex-ether-EtOAc (5:2.5:25). An oily product (15.7 g), still impure was obtained.

EXAMPLE 4

1-(3′,4′-Dimethoxyphenyl)-2-amino-7-(4′-methylphenyl)-5-heptanone ethylene ketal In a 500 mL 3 necked rb flask equipped with a mechanical stirrer, condensor and addition funnel, a THF solution of 1-(3,4-dimethoxyphenyl)-2-nitro-7-(4-methylphenyl)-5-heptanone ethylene ketal (15.7 g; 0.037 mole) was added slowly to a suspension of LiAlH$_4$ (14.2 g; 0.111 mole) in dry THF. The reaction was refluxed for 2 hours. Excess LiAlH$_4$ was then decomposed with sat. Na$_2$SO$_4$, the salts filtered and the organic layer dried over MgSO$_4$, filtered and concentrated to yield 14.2 g of a brown oil.

EXAMPLE 5

2-(3′,4′-Dimethoxybenzyl)-5(2-[4′-methylphenyl]ethyl)-Δ$^{1(5)}$-pyrroline

The above 1-(3,4-dimethoxyphenyl)-2-amino-7-(4-methylphenyl)-5-heptanone ethylene ketal (14.2 g; 0.0356 m), 7.5 g p-toluenesulfonic acid and 100 mL THF were combined and stirred 24 hours at room temperature under nitrogen. The reaction was poured cautiously into 200 mL cold, sat'd NaHCO$_3$ and extracted with three 200 mL portions of ethyl acetate. The organic layer was dried over MgSO$_4$, filtered and concentrated. Chromatography of the crude brown oil on silica gel using CHCl$_3$:ethyl acetate (1:1) gave 7.0 g (0.0188 m) of a brown oil.

EXAMPLE 6

2-(3′,4′-Dimethoxybenzyl)-5-(2-[4′-methylphenyl]ethyl)pyrrolidine 2-(3′4′-dimethoxybenzyl)-5-(2-[4-methylphenyl]ethyl)-Δ$^{1(5)}$-pyrroline (7 g; 0.0188 moles) was hydrogenated in a Parr shaker with PtO$_2$ (0.300 g) in 50 mL methanol at 65 psi.

The catalyst was filtered through Celite and the methanol concentrated. The residue was then triturated with ethyl acetate and di-isopropyl ether. Upon standing 2.4 g (0.0064 mole) of a grey solid was obtained.

EXAMPLE 7

2-(3′,4′-Dihydroxybenzyl)-5-(2-[4′-methylphenyl]ethyl)pyrrolidine hydrobromide

In a 100 mL rb flask equipped with magnetic stirrer and addition funnel, 2-(3′,4′-dimethoxybenzyl)-5-(2-[4′-methylphenyl]ethyl)pyrrolidine (2.4 g; 0.0064M) was dissolved in CH$_2$Cl$_2$ and cooled to −70° C. Boron tribromide (0.024 mole; 6 g) was added cautiously dropwise and the reaction warmed slowly to room temperature over 2.5 h. under N$_2$. The reaction was cooled again to −70° and methanol was added very cautiously until fuming subsided. The solution was then concentrated in vacuo and the residue treated with ethyl acetate. Crystallization occurred upon standing, mp 164°–167°.

EXAMPLE 8

1-(3′,4′-dimethoxyphenyl)-7-phenyl-2-nitro-5-heptanone

To a solution of 36 g (0.17 mole) of 2-(3,4-dimethoxyphenyl)-1-nitroethane in 300 mL of dry tetrahydrofuran was added 71 g (0.17 mole) of 40% Triton B. The solution was stirred at room temperature for 10 min. 55.3 g (0.19 mole) of 1-iodo-5-phenyl-3-pentanone in a minimum amount of dry tetrahydrofuran was added dropwise. The mixture was stirred at room temperature for 30 min, at 50° C. for 3 hr., then allowed to stir at room temperature overnight. Solvent was removed in vacuo and the residue taken up in ether and extracted twice with water. The organic layer was dried over anh MgSO$_4$, and concentrated at reduced pressure to give 71.5 g of crude oil. This crude material was passed through HPLC to give 46.4 g. of purified material.

EXAMPLE 9

1-(3′,4′-dimethoxyphenyl)-7-phenyl-2-nitro-5-heptanone ethylene ketal

Into a 1 l r.b. flask equipped with a Dean Stark trap was placed 46.4 g (0.12 m) of 1-(3′,4′-dimethoxyphenyl)-7-phenyl-2-nitro-5-heptanone, 1.5. g p-toluenesulfonic acid, 50 mL of ethylene glycol and 300 mL of cyclohexane. The mixture was allowed to reflux overnight, then concentrated in vacuo. Dil NaHCO$_3$ solution was added to the residue and extracted with ethyl acetate. The organic layer was backwashed with water, dried over anh. MgSO$_4$, filtered and concentrated under reduced pressure to give 45.3 g of an oil which solidified on drying at room temperature under vacuum.

EXAMPLE 10

2-Amino-1-(3′,4′-dimethoxyphenyl)-7-phenyl-5-heptanone ethylene ketal

To a suspension of 12.4 g (0.33 mole) of LiAlH$_4$ in 500 mL of dry tetrahydrofuran was added dropwise a solution of 45.3 g (0.11 mole) of 1-(3′,4′-dimethoxyphenyl)-7-phenyl-2-nitro-5-heptanone ethylene ketal in a minimum amount of dry tetrahydrofuran. After the addition, the reaction mixture was refluxed gently for 2 hours. The excess LiAlH$_4$ was decomposed with saturated Na$_2$SO$_4$ solution. The inorganic salts were filtered off and washed with ether. The organic layer was extracted twice with water, dried over anh. MgSO$_4$, filtered, and concentrated under reduced pressure to 250 mL. This was used in the next step.

EXAMPLE 11

2-(3′,4′-dimethoxybenzyl)-5-(2-phenethyl)-Δ$^{1(5)}$pyrroline

To the above 250 ml solution of crude 2-amino-1-(3′,4′-dimethoxyphenyl)-7-phenyl-5-heptanone ethylene ketal was added 38 g of p-toluenesulfonic acid. The solution was stirred under a nitrogen atmosphere overnight. The resulting solution was poured slowly into dil NaHCO$_3$ solution and extracted with ether-ethyl acetate. The organic layer was extracted twice with H$_2$O, dried over anh. MgSO$_4$, filtered and concentrated under reduced pressure to give 29.2 g. The crude material was further purified by HPLC to give 18.4 g oil.

EXAMPLE 12

2-(3',4'-Dimethoxybenzyl)-5-(2-phenylethyl)pyrrolidine

To a suspension of 10.8 g (0.28 mole) of LiAlH$_4$ in 500 ml of dry tetrahydrofuran was added dropwise a solution of 18.4 g (0.057 mole) of 2-(3',4'-dimethoxybenzyl)-5-(2-phenylethyl)-$\Delta^{1(5)}$pyrroline in a minimum amount of dry tetrahydrofuran. After the addition, the reaction mixture was refluxed gently for 8 h. The excess LiAlH$_4$ was decomposed with saturated Na$_2$SO$_4$ solution. The inorganic salts were filtered off and washed with ethyl acetate. The organic layer was extracted twice with H$_2$O, dried over anh. MgSO$_4$, filtered and concentrated under reduced pressure to give 15.1 g oil.

EXAMPLE 13

2-(3',4'-Dihydroxybenzyl)-5-(2-phenylethyl)pyrrolidine hydrobromide

To a cold (−70° C.) solution of 15.1 g (0.057 mole) of 2-(3',4'-dimethoxybenzyl)-5-(2-phenylethyl)pyrrolidine in 1 L of methylene chloride was added dropwise 55.1 g (0.22 mole) of boron tribromide. After the addition the reaction mixture was gradually warmed up to room temperature over a period of 2 h. The mixture was cooled again to −70° C. and 300 ml. of methanol was carefully added. Solvent was removed in vacuo. An additional 100 ml of methanol was added and removed in vacuo. The gummy dark residue was boiled in ethyl acetate and decanted, then triturated with ethyl acetate and left overnight to give a solid. This was recrystallized twice from acetonitrile to give 6 g. m.p. 149°–151° C.

EXAMPLE 14

1-(3',4'-Dimethoxyphenyl)-7-(4'-fluorophenyl)-2-nitro-5-heptanone

To a solution of 48.5 g (0.23 mole) of 2-(3',4'-dimethoxyphenyl)-1-nitroethane in 400 ml of dry tetrahydrofuran was added 96.0 (0.23 mole) of 40% Triton B. The solution was stirred at room temperature for 10 minutes. 66.7 g (0.23 mole) of 1-iodo-5-(4'-fluorophenyl)-3-pentanone in a minimum amount of dry tetrahydrofuran was added dropwise. The mixture was heated at 50° C. for 3 hours, then allowed to stir at room temperature overnight. Solvent was removed in vacuo and the residue taken up in ether and extracted twice with water. The organic layer was dried over anh MgSO$_4$, filtered and concentrated at reduced pressure to obtain a crude oil. The crude material was passed through HPLC to give 79 g purified material.

EXAMPLE 15

1-(3',4'-Dimethoxyphenyl)-7-(4'-fluorophenyl)-2-nitro-5-heptanone ethylene ketal Into a 1 l. r.b. flask equipped with a Dean-Stark trap was placed 79 g (0.2 mole) of 1-(3',4'-dimethoxyphenyl)-7-(4'-fluorophenyl)-2-nitro-5-heptanone, 38 g p-toluenesulfonic acid, 120 ml ethylene glycol and 400 ml cyclohexane. The mixture was allowed to reflux overnight, then concentrated in vacuo. Dil NaHCO$_3$ solution was added to the residue and extracted with methylene chloride. The organic layer was backwashed with water, dried over anh MgSO$_4$, filtered and concentrated under reduced pressure to obtain 84.8 g of oily product.

EXAMPLE 16

2-Amino-1-(3',4'-dimethoxyphenyl)-7-(4'-fluorophenyl)-5-heptanone ethylene ketal To a suspension of 22.0 g (0.58 mole) of LiAlH$_4$ in 400 ml of dry tetrahydrofuran was added dropwise a solution of 84.8 g (0.2 mole) of 1-(3',4'-dimethoxyphenyl)-7-(4'-fluorophenyl)-2-nitro-5-heptanone ethylene ketal in a minimum amount of dry tetrahydrofuran. After the addition the reaction mixture was refluxed gently for 2 hours. The excess LiAlH$_4$ was decomposed with saturated Na$_2$SO$_4$ solution. The inorganic salts were filtered off and washed with ether. The organic layer was extracted twice with water, dried over anh MgSO$_4$, filtered and concentrated under reduced pressure to 250 ml. This was used in the next step.

EXAMPLE 17

2-(3',4'-Dimethoxybenzyl)-5-[2-(4'-fluorophenyl)ethyl]-$\Delta^{1(5)}$-pyrroline To the above 250 ml solution of crude 2-amino-1-(3',4'-dimethoxyphenyl)-7-(4'-fluorophenyl)-5-heptanone ethylene ketal was added 114 g of p-toluenesulfonic acid. The solution was stirred under a nitrogen atmosphere overnight. The resulting solution was poured slowly into dil NaHCO$_3$ solution and extracted with methylene chloride. The organic layer was extracted twice with water dried over anh MgSO$_4$, filtered and concentrated under reduced pressure. The crude material was further purified by passing through HPLC to give 32.5 g of product.

EXAMPLE 18

2-(3',4'-Dimethoxybenzyl)-5-[2-(4'-fluorophenethyl)-pyrrolidine

To a suspension of 18 g (0.47 mole) of LiAlH$_4$ in 400 ml of dry tetrahydrofuran was added dropwise a solution of 32.5 g (0.095 mole) of 2-(3',4'-dimethoxybenzyl)-5-[2-(4'-fluorophenyl)ethyl]-$\Delta^{1(5)}$pyrroline in a minimum amount of dry tetrahydrofuran. After the addition, the reaction mixture was refluxed gently for 2 hours. The excess LiAlH$_4$ was decomposed with saturated Na$_2$SO$_4$ solution. The inorganic salt was filtered off and washed with tetahydrofuran and ether. The organic layer was extracted twice with H$_2$O, dried over MgSO$_4$, filtered and concentrated under reduced pressure to give 31.48 g.

EXAMPLE 19

2-(3',4'-Dihydroxybenzyl)-5-[4'-fluorophenyl)ethyl]-pyrrolidine hydrobromide

To a cold (−70° C.) solution of 31.4 g (0.091 mole) of 2-(3',4'-dimethoxybenzyl)-5-[4'-fluorophenyl)ethyl]pyrrolidine in 600 cc of methylene chloride was added dropwise 45.8 g (0.18 mle) of boron tribromide. After the addition, the reaction mixture was gradually warmed to room temperature over a period of 2 hours. The mixture was cooled again to −70° C. and 300 ml of methanol was carefully added. Solvent was removed in vacuo. An additional 100 ml of methanol was added and removed in vacuo. The gummy dark residue was boiled in ethyl acetate and decanted, then triturated with ethyl acetate and left in the refrigerator overnight to give a solid. After recrystallization from a minimum amount of isopropanol this gave 9.05 g, mp 186°–188° C.

EXAMPLE 20

1-(3',4'-Dimethoxyphenyl)-7-(4'-chlorophenyl)-2-nitro-5-heptanone

To a solution of 48.5 g (0.23 mole) of 2-(3,4-dimethoxyphenyl)-1-nitroethane in 400 ml of dry tetrahydrofuran was added 96.0 g (0.23 mole) of 40% Triton B. The solution was stirred at room temperature for 10 min. 70.3 g (0.23 mole) of 5-iodo-1-(4'-chlorophenyl)-3-pentanone in a minimum amount of dry tetrahydrofuran was added dropwise. The mixture was heated at 50° C. for 3 hr., then allowed to stir at room temperature overnight. Solvent was removed in vacuo and the residue taken up in ether and extracted twice with water. The organic layer was dried over anh $MgSO_4$, filtered and concentrated at reduced pressure. The crude concentrate was passed through HPLC to give 65 g of purified material.

EXAMPLE 21

1-(3',4'-Dimethoxyphenyl)-7-(4'-chlorophenyl)-2-nitro-5-heptanone ethylene ketal Into 1 l. r.b. flask equipped with a Dean Stark trap was placed 65 g (0.16 mole) of 1-(3',4'-dimethoxyphenyl)-7-(4'-chlorophenyl)-2-nitro-5-heptanone, 2 g p-toluenesulfonic acid, 100 ml ethylene glycol and 400 ml of cyclohexane. The mixture was allowed to reflux overnight, then concentrated in vacuo. Dil $NaHCO_3$ solution was added to the residue and extracted with methylene chloride. The organic layer was backwashed with water, dried over anh $MgSO_4$, filtered and concentrated under reduced pressure to obtain 45.3 g of an oil which solidified on drying at room temperature under vacuum.

EXAMPLE 22

2-Amino-1-(3',4'-dimethoxyphenyl)-7-(4'-chlorophenyl)heptan-5-one ethylene ketal To a suspension of 16.5 g (0.43 mole) of $LiAlH_4$ in 500 ml of dry tetrahydrofuran was added dropwise a solution of 65 g (0.14 mole) of 1-(3',4'-dimethoxyphenyl)-7-(4'-chlorophenyl)-2-nitroheptan-5-one ethylene ketal in a minimum amount of dry tetrahydrofuran. After the addition the reaction mixture was refluxed gently for 2 hrs. The excess $LiAlH_4$ was decomposed with saturated $MgSO_4$ solution. The inorganic salts were filtered off and washed with ether. The organic layer was extracted twice with water, dried over anh $MgSO_4$, filtered and concentrated under reduced pressure to 250 ml. This was used in the next step.

EXAMPLE 23

2-(3',4'-Dimethoxybenzyl)-5-(2-(4-chlorophenyl)ethyl)-$\Delta^{1(5)}$-pyrroline

To the above 250 ml solution of crude 2-amino-1-(3,4-dimethoxyphenyl)-7-(4-chlorophenyl)-5-heptanone ethylene ketal was added 5.7 gms of p-toluenesulfonic acid. The solution was stirred under a nitrogen atmosphere overnight. The resulting solution was poured slowly into dil $NaHCO_3$ solution and extracted with methylene cloride. The organic layer was extracted twice with $H_2O$, dried over anh $MgSO_4$, filtered and concentrated under reduced pressure. The crude material was further purified by passing through HPLC to give 26.2 gm.

EXAMPLE 24

2-(3',4'-Dimethoxybenzyl)-5-(2-(4-chlorophenyl)ethyl)-pyrrolidine

To a suspension of 13.9 g (0.36 mole) of $LiAlH_4$ in 400 ml of dry tetrahydrofuran was added dropwise a solution of 26.2 g (0.073 mole) of 2-(3',4'-dimethoxybenzyl)-5-[2-(4-chlorophenyl)ethyl]-$\Delta^{1(5)}$-pyrroline in a minimum amount of dry tetrahydrofuran. After the addition the reaction mixture was refluxed gently for 2 hours. The excess $LiAlH_4$ was decomposed with saturated $Na_2SO_4$ solution. The organic salt was filtered off and washed with tetrahydrofuran and ether. The organic layer was extracted twice with $H_2O$, dried over $MgSO_4$, filtered and concentrated under reduced pressure to give 24.2 g.

EXAMPLE 25

2-(3',4'-Dihydroxybenzyl)-5-[2-(4-chlorophenyl)ethyl]-pyrrolidine hydrobromide

To a cold (−70° C.) solution of 24.2 g (0.67 mole) of 2-(3',4'-dimethoxybenzyl)-5-[2-(4-chlorophenyl)ethyl]-pyrrolidine in 600 cc of methylene chloride was added dropwise 46.5 g (0.186 mole) of boron tribromide. After the addition the reaction mixture was gradually warmed to room temperature over a period of 2 hours. The mixture was cooled again to −70° C. and 300 ml of methanol was carefully added. Solvent was removed in vacuo. An additional 100 ml of methanol was added and removed in vacuo. The gummy residue was boiled in ethyl acetate and decanted, then triturated with ethyl acetate and left in the refrigerator overnight to give a solid. After recrystallization from a minimum amount of methanol there was obtained 7.05 g.

EXAMPLE 26

2-(3',4'-Dimethoxybenzyl)-5-[2-(4'-methoxyphenethyl)]-1-benzylpyrrolidine

To a solution of 2-(3',4'-dimethoxybenzyl)-5-[2-(4'-methoxyphenthkyl)]pyrrolidine hydrochloride in 50 ml dry tetrahydrofuran and 25 ml dry dimethylformamide was added 0.96 g (0.02 mole) of 50% NaH. The reaction mixture was heated at 60° C. for 4 hours. 1.71 g (0.01 mole) of benzyl bromide was added slowly. After the addition the reaction was heated at 50° C. for 2 hours, then stirred overnight. Solvent was removed in vacuo and the residue taken up in methylene chloride and extracted twice with $H_2O$. The organic layer was dried over anh $MgSO_4$, filtered and concentrated at reduced pressure to give 4.4 g of crude material.

EXAMPLE 27

1-Benzyl-2-(3',4'-dihydroxybenzyl)-5-[2(4'-hydroxyphenyl)ethyl]pyrrolidine hydrobromide To a cold (−70° C.) solution of 4.4 g (0.01 mole) of 2-(3',4'-dimethoxybenzyl)-5-[4'-methoxyphenyl)ethyl]-1-benzylpyrrolidine in 100 ml methylene chloride was added dropwise 10 g (0.04 mole) of boron tribromide. After the addition the reaction mixture was stirred at −70° C. for 1 hour then at room temperature for 1.5 hours. The mixture was cooled again to −70° C. and 100 cc of methanol was carefully added. Solvent was removed in vacuo. The residue was redissolved in 30 ml of ethyl acetate-acetone and concentrated. Further drying under high vacuum gave 4.4 g of crude solid.

EXAMPLE 28

2(3',4'-bis-[3,3-Dimethylbutyryloxy]benzyl)-5-[2-(4'-[3,3-dimethylbutyryloxy]phenyl)ethyl]-1-benzylpyrrolidine To a solution of 4.0 g (0.008 mole) of 2-(3',4'-dihydroxybenzyl)-5-[2-(4'-hydroxyphenyl)ethyl]-1-benzylpyrrolidine hydrobromide in 50 ml pyridine was added dropwise 4 g (0.03 mole) of 3,3-dimethylbutyryl chloride. After the addition, the reaction mixture was stirred at room temperature for 1 hour, then at 70° C. for 1.5 hours, and finally at room temperature overnight. The salt was filtered and solvent was removed in vacuo. The residue was taken up in methylene chloride and extracted twice with dil NaHCO$_3$ solution. The organic layer was dried over anh MgSO$_4$, filtered and concentrated at reduced pressure. The crude material was further purified by HPLC to give 2 g.

EXAMPLE 29

2-(3',4'-bis[3,3-Dimethylbutyryloxy]benzyl)-5-[2-(4'-[3,3-dimethylbutyryloxy]phenyl)ethyl]pyrrolidine A mixture of 2 g (0.0028 mole) of 2-(3',4'-bis[3,3-dimethylbutyryloxy]benzyl)-5-[2-(4'-[3,3-dimethylbutyryloxy]phenyl)ethyl]-1-benzylpyrrolidine and 0.2 g 10% Pd/C in 100 methanol was hydrogenated at 60 psi in a Parr hydrogenator overnight. This catalyst was filtered off and the filtrate concentrated under reduced pressure to give 1.7 g. The crude material was purified by HPLC to give 0.93 g thick oil.

EXAMPLE 30

2-(4'-Hydroxybenzyl)-5-[2-(4'-methoxyphenyl)ethyl]-pyrrolidine

A mixture of 11 g (0.027 mole) of 2-(4'-benzyloxybenzyl)-5-[2-(4'-methoxyphenyl)ethyl]pyrrolidine and 0.5 g 10% PdC in 200 ml of methanol was hydrogenated at 45 psi in a Parr hydrogenator for 48 hours. The catalyst was filtered off and the filtrate was concentrated under reduced pressure to give 7.6 g crude material.

EXAMPLE 31

2-(4'-Hydroxybenzyl)-5-[2-(4'-hydroxyphenyl)ethyl]-pyrrolidine hydrobromide

To a cold (−70° C.) solution of 2 g (0.006 mole) of 2-(4'-hydroxybenzyl)-5-[2-4'-methoxyphenyl)ethyl]pyrrolidine in 150 ml methylene chloride was added dropwise 2.5 g (0.01 mole) of boron tribromide. After the addition the reaction mixture was stirred at −70° C. for 1 hour, then at room temperature for 1 hour. The mixture was cooled again to −70° C. and 50 ml of methanol was carefully added. Solvent was removed in vacuo. The residue was triturated with 30 ml ethyl acetate which was decanted. The residue was again triturated with 30 ml acetone to give a solid which was recrystallized from a minimum amount of ethanol to give 560 mg, mp 177°-179° C.

EXAMPLE 32A 2-(3,4-Dimethoxybenzoyl)-6-methylpyridine

To an ice-cooled, stirred suspension of 6-methylpicolinic acid chloride and 2 equivalents of aluminum chloride in tetrachloroethane is added slowly an equivalent amount of 1,2-dimethoxybenzene. The reaction mixture is allowed to come to room temperature overnight, then decomposed over cracked ice. Extractive workup followed by chromatography of the organic residue gives the desired ketone.

EXAMPLE 32B 2-(3,4-Dimethoxybenzoyl)-6-(2-(4-methoxyphenyl)ethyl)piperidine

The above ketone is condensed with anisaldehyde using the general procedure of Galiazzo, GAZZ. CHIM. ITAL., 95, 1322, (1965). Chromatography of the basic material gives the desired stilbazole.

The stilbazole is dissolved in glacial acetic acid and hydrogenated over Adams' catalyst at 2–3 atm until four equivalents of hydrogen have been absorbed. The reaction is filtered, concentrated, and washed with aqueous base to remove the last traces of acetic acid. Chromatography over silica gel then gives the desired piperidine.

EXAMPLE 32C

2(α-Hydroxy-3,4-dimethoxybenzyl)-6-(2-(4-methoxyphenyl)ethyl)piperidine

The above amino ketone is dissolved in ethanol, cooled in ice, and treated with one equivalent of sodium borohydride. Upon appearance of starting material (TLC) the reaction is diluted with water and extracted with ethyl acetate. The extracts are washed with water, dried, and concentrated. Fractional crystallization of the derived hydrochloride gives the major diastereomer.

EXAMPLE 33A 2-(3,4-Dimethoxybenzyl)-6-(2-(4-methoxyphenyl)ethyl)piperidine

The amino alcohol of Example 32C is dissolved in ethanol and hydrogenated over 10% Pd-C until no further uptake occurs. The solution is then filtered, concentrated, and chromatographed to give the title trimethoxy compound.

EXAMPLE 33B 2-(3,4-Dihydroxybenzyl)-6-(2-(4-hydroxyphenyl)ethyl)piperidine hydrobromide The above trimethoxy compound is treated with BBr$_3$ in the manner of Ex. 2. Evaporation of boron compounds and trituration of the residue as described gives the desired salt.

EXAMPLE 34

2-(α,3,4-Trihydroxybenzyl)-6-(2-(4-hydroxyphenyl)ethyl)piperidine hydrobromide

The trimethoxy alcohol of Ex. 32C is treated with excess BBr$_3$ in dichloromethane as described in Ex. 2. Evaporation of boron compounds with methanol and trituration of the non-volatile material gives the title salt.

EXAMPLE 35A (6-Methyl-1-carbobenzyloxy-2-piperidyl)oxirane

A solution of 2-methyl-6-ethenyl-1-piperidyl benzyl urethane in methylene chloride is cooled to 0° C. and treated with one equivalent of m-chloroperoxybenzoic acid. After stirring at room temperature until disappearance of starting material the peracid is decomposed with sodium bisulfite and the mixture washed with aqueous Na$_2$CO$_3$. The product is used directly.

EXAMPLE 35B

2-Methyl-6-(2-(4-fluorophenyl)oxy-1-hydroxyethyl)-piperidine

A solution of a p-fluorophenol in t-butanol is treated with one equivalent of potassium t-butoxide, followed by the compound of Example 35A. The reaction mixture is then refluxed until all epoxide has reacted. The reaction is cooled, diluted with water, and extracted with ethyl acetate. The organic extracts are dried and concentrated. The carbobenzyloxy protecting group is removed by standard hydrogenolysis and the final product purified by chromatography.

Using the procedure of Examples 1, 2, 32 and 33, the following cyclic amines of Formulae I and II are prepared from the corresponding dehydro compounds of Formulae V and VI:

2-(3,4-Dihydroxybenzyl)-5-[2-(4-chlorophenyl)ethyl]-pyrrolidine
2-(3,4-Dihydroxybenzyl)-5-[2-(4-fluorophenyl)ethyl]-pyrrolidine
2-(3,4-Dihydroxybenzyl)-5-(2-phenylethyl)pyrrolidine
2-(3,4-Dimethoxybenzyl)-6-[2-(4-methoxyphenyl)ethyl]piperidine
2-(3,4-Dihydroxybenzyl)-6-[2-(4-hydroxyphenyl)ethyl]piperidine
2-(3,4-Dihydroxybenzyl)-6-[2-(4-chlorophenyl)ethyl]-piperidine
2-(3,4-Dihydroxybenzyl)-6-[2-(4-fluorophenyl)ethyl]-piperidine
2-(3,4-Dihydroxybenzyl)-6-(2-phenylethyl)piperidine
2-(4-Hydroxybenzyl)-5-[2-(4-hydroxyphenyl)ethyl]pyrrolidine
2-(3,4-Dihydroxybenzyl)-5-[2-(4-trifluoromethylphenyl)ethyl]pyrrolidine
2-(3,4-Dihydroxybenzyl)-6-[2-(4-chlorophenyl)ethyl]-piperidine
2-(3,4-Dihydroxybenzyl)-6-[2-(4-fluorophenyl)ethyl]-piperidine
2-(3,4-Dihydroxybenzyl)-6-(2-phenylethyl)piperidine
2-(4-Hydroxybenzyl)-6-[2-(4-hydroxyphenyl)ethyl]-piperidine
2-(3,4-Dihydroxybenzyl)-6-[2-(4-trifluoromethylphenyl)ethyl]piperidine
2-[2-Hydroxy-3(3,4-dihydroxyphenyloxy)propyl]-6-[2-(4-hydroxyphenyl)ethyl]piperidine
2-[2-Hydroxy-3-(3-fluoro-4-hydroxyphenyloxy)-propyl]-6-[2-(4-hydroxyphenyl)ethyl]piperidine

We claim:

1. A method for increasing cardiac contractility which comprises administering to a mammal in need of such treatment a cardiotonically effective amount of a composition comprising in combination with a pharmaceutically acceptable carrier a compound of the formula

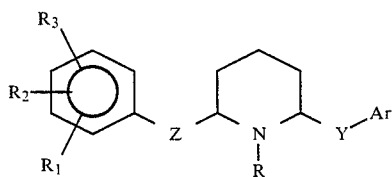

or a pharmaceutically acceptable acid addition salt thereof wherein,

Z and Y are each alkylene containing one to about five carbon atoms in the principal chain or said alkylene substituted with OH, alkanoyloxy;

each of $R_1$, $R_2$ and $R_3$ is independently H, alkyl, halo, alkoxy, alkylsulfinyl, alkylmercapto, cyano, carboxy, carbalkoxy, sulfamoyl, trifluoromethyl, hydroxy, hydroxyalkyl, or lower-alkanoyloxy; or $R_1$ and $R_2$, when taken together, form a methylenedioxy or —O—CO—O—;

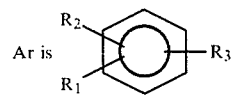

wherein, $R_1$, $R_2$ and $R_3$ are as herein described; and

R is H, alkyl, cycloalkyl, alkenyl, alkynyl, carbalkoxy, or $CONR_4R_5$ wherein each of $R_4$ and $R_5$ is H or alkyl; wherein the total number of carbon atoms in each hydrocarbyl group is up to 6.

2. A method for increasing cardiac contractility which comprises administering to a mammal in need of such treatment a cardiotonically effective amount of a composition comprising in combination with a pharmaceutically acceptable carrier a compound of the formula:

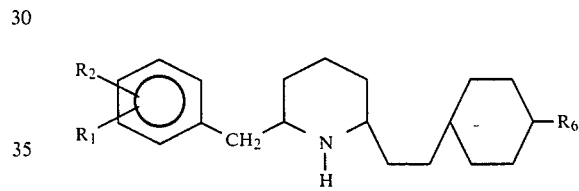

or a pharmaceutically acceptable acid addition salt thereof, wherein, each of $R_1$ and $R_2$ is independently H, alkyl, halo, alkoxy, alkylsulfinyl, alkylmercapto, cyano, carboxy, carbalkoxy, sulfamoyl, trifluoromethyl, hydroxy, hydroxyalkyl, or lower-alkanoyloxy; and $R_1$ and $R_2$, when taken together, form a methylenedioxy, or —O—CO—O—; $R_6$ is H, alkyl, halo, alkoxy, alkylmercapto, cyano, carboxy, carbalkoxy, sulfamoyl, trifluoromethyl, hydroxy, hydroxyalkyl, or lower-alkanoyloxy; wherein the total number of carbon atoms in each hydrocarbyl group is up to 6.

3. A method for increasing cardiac contractility which comprises administering to a mammal in need of such treatment a cardiotonically effective amount of a composition according to claim 2 wherein said compound is

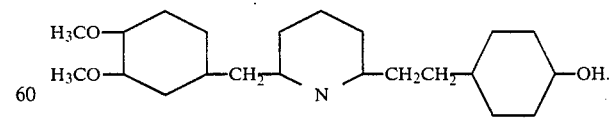

4. A method for increasing cardiac contractility which comprises administering to a mammal in need of such treatment a cardiotonically effective amount of a composition comprising in combination with a pharmaceutically acceptable carrier a compound of the formula

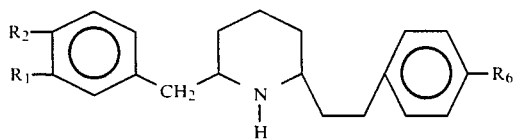
wherein $R_1$, $R_2$ and $R_6$ are independently hydroxy or alkanoyloxy, wherein the alkyl portion of the alkanoyloxy contains up to 6 carbon atoms.
* * * * *